(12) United States Patent
Dolphin et al.

(10) Patent No.: US 6,613,304 B2
(45) Date of Patent: Sep. 2, 2003

(54) RADIOMETAL COMPLEXES OF 2-PYRROLYLTHIONES AND THEIR USE AS RADIOPHARMACEUTICALS FOR IMAGING AND THERAPY

(75) Inventors: David H. Dolphin, Vancouver (CA); Svetlana V. Kudrevich, Outremont (CA); Svetlana V. Selivanova, Fleurimont (CA); Jacques Rousseau, Sherbrooke (CA); Johannes E. Van Lier, North Hatley (CA)

(73) Assignees: University of British Columbia (CA); Universite de Sherbrooke (CA)

( * ) Notice: Subject to any disclaimer, the term of this patent is extended or adjusted under 35 U.S.C. 154(b) by 0 days.

(21) Appl. No.: 09/839,618

(22) Filed: Apr. 20, 2001

(65) Prior Publication Data

US 2002/0102209 A1 Aug. 1, 2002

Related U.S. Application Data

(60) Provisional application No. 60/198,615, filed on Apr. 20, 2000.

(51) Int. Cl.$^7$ ................................................ A61K 51/00
(52) U.S. Cl. ........................... 424/1.65; 534/10; 534/14
(58) Field of Search ........................... 424/1.65; 534/10, 534/11, 14; 548/400, 402, 403, 404

(56) References Cited

PUBLICATIONS

Bruckner, C. et al. (2000) *Inorg Chem* 39:6100–6106.
Selivanova, S. et al. (2000) *J of Nuclear Medicine* 5(suppl) 41:149P, AN587.
Selivanova, S. et al. (2001) *Bioorg & Med Chemistry Letters* 11:2697–2699.
Blower et al., J. Nucl. Med. (1990) 31:768.
Bruckner et al., J. Porphyrins Phtalocyanines (1998) 2:455.
Bubeck et al., J. Nucl. Med. (1990) 31:1285–1293.
Chervu et al., J. Nucl. Med. (1984) 25:1111–1115.
Clezy and Smythe, Aust. J. Chem. (1969) 22:239.
Dilworth et al., Chemical Society Reviews (1998) 27:42–55.
Fritzberg et al., J. Nucl. Med. (1996) 27:111–116.
Gianolli et al., Nucl. Med. Biol. (1996) 23:927–933.
Herzog et al., J. Nucl. Med. (1992) 33:2190–2195.
Jurisson et al., Chem. Rev. (1993) 93:1137–1156.
Knapp et al., Chemical Communications (1973) March issue:149–151.
Pesson et al., Chimie Therapeutique (1966) 3:127–136.
Taylor et al., Radiology (1987) 162:365–370.
Vanbilloen et al., Eur. J. Nucl. Med. (1997) 24:1374–1379.
Verbruggen et al., Technetium and Rhenium in Chemistry and Nuclear Medicine, (M. Nicolini, G. Bandoli, U. Mazzi, eds.), Verona: cortina International, pp. 445–452 (1990).

*Primary Examiner*—Michael G. Hartley
(74) *Attorney, Agent, or Firm*—Morrison & Foerster LLP

(57) ABSTRACT

Novel 2-pyrrolylthione derived metal chelate compounds are disclosed as imaging and therapeutic agents. Compositions and methods for their preparation and use as diagnostic imaging and therapeutic agents are also disclosed.

19 Claims, 8 Drawing Sheets

RADIOMETAL COMPLEXES OF 2-PYRROLYLTHIONES AND THEIR USE AS RADIOPHARMACEUTICALS FOR IMAGING AND THERAPY

RELATED APPLICATIONS

The present application claims benefit of priority from U.S. Provisional Patent Application 60/198,615 filed Apr. 20, 2000, which is hereby incorporated by reference in its entirety as if fully set forth.

FIELD OF THE INVENTION

The invention is in the field of diagnostic imaging and therapeutics. It relates to novel metal chelates containing metal species bound by 2-pyrrolylthione core in $N_2S_2$ fashion. Methods for the preparation of the chelate complexes are provided. The invention also provides pharmaceutical compositions comprising the metal chelate, and the use of this composition as a diagnostic imaging or therapeutic agent. Kits comprising the compounds and compositions of the invention are also provided.

BACKGROUND OF THE RELATED ART

The art of diagnostic imaging employs contrasting agents that in binding or accumulating site-specifically within the body help to resolve the image of diagnostic interest.

For example, renography using radiotracers is the method of choice that allows the determination of both total and differential renal function and the detection of obstructions in urine flow. For this purpose, a composition comprising the radiopharmaceutical, such as an injectable liquid, is administered to the patient. By means of a suitable detection apparatus, such as a camera for detecting radiodecay, images can be obtained by recording the emitting radiation. Thus the organ or the pathological process in which the radiopharmaceutical has been incorporated may be visualized.

Among the oldest and most widely employed techniques for renal function evaluation are the renal clearance methods; the most fundamental of which is directed toward determination of glomerular filtration rate (GFR). In addition, the clearance of compounds that undergo extensive tubular excretion in addition to filtration allow the evaluation of functional tubular mass and the estimation of effective renal plasma flow (ERPF).

The standard for ERPF determination is p-aminohippurate (PAH), of which approxymately 90% is extracted from the renal arterial plasma in a single pass through the renal parenchyma. An I-131 labeled structural analog, ortho-iodohippurate ([$^{131}$I]OIH; Hippuran), has been the clinical standard for the past 30 years. Although OIH yields a good approximation of renal plasma flow, the 364 keV photon energies of I-131 results in poor spatial resolution and the emission of beta partcles increases the radiation dose to the patient. Labeling OIH with I-123 results in a better imaging agent, but the availability and prohibitively high cost of I-123 limits the use of this compound.

Because of the favorable physical properties, widespread availability, and low cost of technetium-99m (Tc-99m), this radionuclide continues to be the most attractive candidate for the formulation of diagnostic radiopharmaceuticals to be used in scintigraphic gamma-imaging studies in patients (Jurisson et al., "Coordination compounds in nuclear medicine". Chem.Rev. 93:1137–1156 (1993)).

[$^{99m}$Tc]TcO(glucoheptonate)$_2$, Glucoscan, also known as Technescan, is an early kidney imaging agent, the precise structure of which has never been determined. While this complex is no longer widely used as an imaging agent; however, it is regularly used as a precursor for the synthesis of other Tc(V) species via ligand exchange.

[$^{99m}$Tc]Tc-diethylenetriaminepentaacetic acid (or [$^{99m}$Tc]Tc-DTPA) has received regulatory approval for use as a kidney imaging agent. The structure of this complex has not yet been determined unequivocally, and it is unclear as to whether the complex contains technetium in the IV or V oxidation state. This radiopharmaceutical has very limited clinical applications.

Early attempts to create a Tc-99m-based renal imaging agent focussed on the diamine dithiolate (DADT) ligands. $^{99m}$Tc-N,N'-bis(mercaptoacetyl)-2,3-diaminopropanoate ($^{99m}$Tc-CO$_2$DADS) (Fritzberg et al., "Synthesis and biological evaluation of Tc-99m-N,N'-bis(mercaptoacetyl)-2,3-diaminopropanoate: A potential replacement for [I-131]-o-iodohippurate" 23:592–598 (1982)) has a favorable renal clearance profile, but this compound consists of stereoisomers with different rates and specificities for renal clearance. Therefore, HPLC separation of the desired stereoisomer is required, which makes routine preparation inconvenient.

The para-aminohippuric (PAH) acids have been found to be almost completely extracted from blood flow by the kidneys. Incorporation of an iminodiacetic acid (IDA) moiety into PAH yielded p-[(biscarboxymethylaminomethyl) carbamino]hippuric acid (PAHIDA) with a clearance of less than 50% of OIH (Chervu et al., "Technetium-99m labeled p-aminohippuric acid analog: A new renal agent" J. Nucl. Med. 25:1111–1115 (1984)).

Later, the triamide mercaptide (N$_3$S) class of Tc-99m-chelating agents was developed (Fritzberg et al., "Synthesis and biological evaluation of Tc-99m-MAG$_3$ as a hippuran replacement" J. Nucl. Med. 27:111–116 (1986)). To date, the $^{99m}$Tc-mercaptoacetyltriglycine ([$^{99m}$TcO-MAG$_3$]$^-$) is considered to be one of the most successful agents for functional renal imaging. A few minutes post injection, approximately 1–2% of the injected dose of Tc-99m-MAG$_3$ is found in the kidneys. At the same time, this drug is cleared from the kidney tissue very rapidly. It is the passage into and through the kidneys that provides a measure of renal function (ERPF). Although considered to be the renal imaging agent of choice, Tc-99m-MAG$_3$ is not free of certain problems associated with its use. For instance, the plasma-protein binding of Tc-99m-MAG$_3$ is very high (Taylor et al., Radiology. 162:365–370 (1987); and Bubeck et al., J Nucl. Med. 31:1285–1293 (1990)); the clearance of Tc-99m-MAG$_3$ is only 50–60% of that of OIH and therefore is not suitable for direct measurement of ERPF. In addition, the preparation of Tc-99m-MAG$_3$ requires the kit to be heated at 100° C. for 10 min, thus adding an inconvenient step in the preparation.

It was found (Verbruggen et al., "Technetium and rhenium in chemistry and nuclear medicine", vol.3 (M. Nicolini, G. Bandoli, U. Mazzi, eds.). Verona: Cortina International, pp. 445–452 (1990)) that the polar metabolite of the brain radiopharmaceutical, diethyl Tc-99m-ethylenedicysteine (Tc-99m-L,L-EC), was rapidly and efficiently excreted by the kidneys in mice. This observation prompted the evaluation of Tc-99m-L,L-EC as a potential renal imaging agent. Studies in mice and baboons showed that the pharmacokinetic properties of Tc-99m-L,L-EC are superior to those of Tc-99m-MAG$_3$. Tc-99m-L,L-EC yields a better approximation of ERPF.

The true test of a new radiopharmaceutical, however, is how it performs in patients with various renal disorders that can cause drastic changes in pharmacokinetics. To date a number of clinical studies have been conducted in patients with a variety of renal disorders comparing Tc-99m-L,L-EC and Tc-99m-MAG$_3$. Generally speaking, between the two tracers, there was no significant difference in the image quality or in the parameters derived from the renogram.

Because of the low chemical stability of the thiol group to oxidation, MAG$_3$ is synthesized and supplied in commercial kits as an S-benzyl protected derivative. After reconstitution the kit must be kept in the dark to prevent oxidation of the thiol.

To circumvent this problem, an attempt was made to substitute a hydroxy group for the thiol in MAG$_3$ (Vanbilloen et al., "Characteristics and biological behavior of Tc-99m-labeled hydroxyacetylglycine, a potential alternative to $^{99m}$Tc-MAG$_3$".; Eur. J. Nucl. Med. 24:1374–1379 (1997)). The resulting Tc-99m-labeled hydroxyacetyltriglycine (HAG$_3$) had a slightly higher urinary excretion and faster renal transit than Tc-99m-MAG$_3$. The faster renal clearance of Tc-99m-HAG$_3$ can be attributed to its lower plasma protein binding—comparable with what was seen with Tc-99m-L,L-EC. Although the renal excretion characteristics of Tc-99m-HAG$_3$ are slightly better than those of Tc-99m-MAG$_3$ and the labeling is done at room temperature, the chemical stability of the Tc-99m-HAG$_3$ to transchelation is less than that of the thiol containing analog.

Certain Tc-99m-labeled molecules have a high extraction rate from the bloodstream by the kidneys in combination with a high retention rate by the kidneys. A radiopharmaceutical of this kind is Tc-99m-dimercaptosuccinic acid (Tc-99m-DMSA; Technetium-99m Succimer Injection). The Tc(III) or Tc(V) complex (of unknown structure) is prepared from the reaction of $^{99m}$TcO$_4^{-1}$ with DMSA in the presence of the reducing agent Sn(II) chloride. Tc-99m-DMSA has a specific affinity for the renal cortex. In healthy subjects, the renal activity increases until 6 to 8 hours after injection at which point, a steady level of uptake is reached representing some 30% of the activity administered. At the plasma level, Tc-99m-DMSA is almost completely bound to the proteins. Tc-99m-DMSA is used in morphological studies of kidneys. Such examinations constitute a useful approach in the diagnosis, location and evaluation of various renal pathologies: inflammation, infection, lithiases, traumatisms, tumors etc. Measurement of the renal fixation of the Tc-99m-DMSA complex also makes it possible to assess overall renal function.

A bidentate chelator N-mercaptoacetylglycine (GAM) has been suggested as a Tc-99m-ligand (Gianolli et al., "$^{99m}$Tc-2GAM: a tracer for renal imaging". Nucl. Med. Biol. 23:927–933 (1996)). GAM contains both a thiolato sulfur and an amido nitrogen similar to MAG$_3$ and DADS, but it is a bidentate ligand similar to DMSA. The resulting 2:1 complex (Tc-99m-2GAM) can adopt either a cis- or trans-configuration relative to the oxotechnetium core. Biodistribution studies in animals and normal volunteers indicate that Tc-99m-2GAM has biological properties which are more similar to Tc-99m-DMSA, rather than to Tc-99m-MAG$_3$ or Tc-99m-DADS. Tc-99m-2GAM activity in the kidney reaches a plateau more rapidly than Tc-99m-DMSA and thus may be a possible replacement for Tc-99m-DMSA.

All the above mentioned imaging agents are organic anions. They are transported by the organic anion receptors in the renal tubular system. A buildup of organic anions in plasma, which happens in patients suffering from uremia, can competitively inhibit renal tubular transport of anionic tracers, thereby leading to artificially low estimates of renographic parameters in uremic patients.

Another tubular transport mechanism—the cationic transporter system—cannot be disrupted by anion accumulation. Tetraazapolyamine chelators, such as cyclam and tetramethylcyclam, were evaluated for their ability to form stable complexes with dioxotechnetium (Herzog et al., "Synthesis and renal excretion of technetium-99m-labeled organic cations" J. Nucl. Med. 33:2190–2195 (1992)). The overall charge of each Tc-99m complex was +1. The magnitude of the plasma protein binding for these organic cations was comparable to that of Tc-99m-EC and significantly less than that of OIH and Tc-99m-MAG$_3$. The renal clearance of tetraazapolyamines was similar to that of Tc-99m-L,L-EC. The mode of excretion of these tracers by the tubule cationic transporter system was clearly identified.

The choice of Tc-99m-radiopharmaceuticals for renal imaging is presently limited to a few small hydrophilic molecules containing mostly N$_2$S$_2$ technetium cores. Within each class of existing kidney radiotracers there are not many possibilities for modifying the periphery of the molecule to fine tune the solubility of the compound and its pharmacokinetics. Therefore, there is a need to develop new Tc-99m ligands which could vary the size and lipophilicity of stable Tc-99m-complexes containing the same type of Tc-core.

SUMMARY OF THE INVENTION

The present invention provides metal chelates which are suitable as pharmacutical imaging agents for various organs and tissues, preferably imaging renal tissues. The metal chelates of this invention have high organ-specificity for kidney tissues. The chelates possess sufficient stability to allow the completion of the preparation of the radiopharmaceutical, as well as a thorough performance of a renal examination.

In particular embodiments of this inventions, the metal chelates based on a 2-pyrrolylthione structure are provided as being suitable as radiopharmaceutical agents and represented by Formula I:

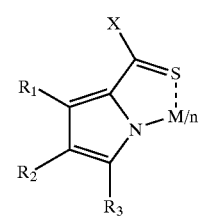

wherein
M is independently selected from the group consisting of radioisotopes of Tc, Re, Cd, Pb, Zn, Ag, Au, Ga, Pt, Pd, Rh, Cr, Cu, V and the like;
n=1 to 4;
R$_1$, R$_2$, and R$_3$ is independently hydrogen, alkyl, OH or its derivative, halogen, NO$_2$, NH$_2$, N$^+$R$_3$, NHCOR, CN, an alkyl carboxylic acid or acid ester group or its derivative, keto, SO$_3$H or its derivative, or a group that, when taken together with another ring, ring substituent, forms a fused 5 or 6 membered ring, wherein R is independently hydrogen, alkyl, OH or its derivative, halogen, CN, an alkyl carboxylic acid or acid ester group or its derivative, keto, or SO$_3$H or its derivative;
unsubstituted or substituted alkyl or heteroalkyl, unsubstituted or substituted carbocycle, including aryl, unsubstituted or substituted heterocycle, AOH, ACOOH, ACOOR, AHal, CN, ANO$_2$, ANH$_2$, ANR$_2$, AN+R₃, and ANHCOR wherein A is alkyl, heteroalkyl, carbocycle, including aryl or heterocycle, and R is alkyl or aryl and Hal is a halogen, preferably F, CL, Br, or I.

Thus the metal chelates also include from one to four 2-pyrrolylthiones bound to a single metal atom or isotope. Moreover, the chelates contain variations in the ligand periphery, encompassed by positions $R_1$, $R_2$, $R_3$, and X above, to contain hydrophilic or lipophilic substituents.

In one aspect of the invention, the di-2-pyrrolylthione-based metal chelates encompassed by Formula I have the desirable characteristics of significant renal uptake and retention. Preferably, such characteristics are comparable, or superior to, that observed with Tc-99m-DMSA (Technetium-99m Succimer Injection). Moreover, the metal chelates of the invention permit the resulting diagnostic image quality to be comparable or superior to that with Tc-99m-DMSA (Technetium-99m Succimer Injection).

In another embodiment of the invention, Tc-99m-chelates encompassed by Formula I are available in high radiochemical purity (>90%) and with high specific activity.

In another aspect of the invention, methods used to synthesize Tc-99m chelates encompassed by Formula I are disclosed. The methods used to purify such radiopharmaceuticals are also described. Furthermore, this invention provides a radiopharmaceutical composition useful for renal imaging and as a therapeutic. Such a radiopharmaceutical composition is comprised of a metal chelate as described above and a pharmaceutically acceptable carrier.

Particular embodiments of this invention provide 2-pyrrolylthione ligands suitable for the formation of metal chelates of Formula I. These ligands are encompassed by the following Formula II:

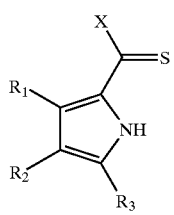

II wherein $R_1$, $R_2$, and $R_3$ is independently hydrogen, alkyl, OH or its derivative, halogen, $NO_2$, $NH_2$, $N^+R_3$, NHCOR, CN, an alkyl carboxylic acid or acid ester group or its derivative, keto, $SO_3H$ or its derivative, or a group that, when taken together with another ring, ring substituent, forms a fused 5 or 6 membered ring, wherein R is independently hydrogen, alkyl, OH or its derivative, halogen, CN, an alkyl carboxylic acid or acid ester group or its derivative, keto, or $SO_3H$ or its derivative;

X is independently selected from the group consisting of unsubstituted or substituted alkyl or heteroalkyl, unsubstituted or substituted carbocycle, including aryl, unsubstituted or substituted heterocycle, AOH, ACOOH, ACOOR, AHal, CN, $ANO_2$, $ANH_2$, $ANR_2$, $AN^+R_3$, and ANHCOR wherein A is alkyl, heteroalkyl, carbocycle, including aryl or heterocycle, and R is alkyl or aryl and Hal is a halogen, preferably F, CL, Br, or I.

Particular embodiments of this invention include 2-pyrrolylthione ligands encompassed by Formula II that are capable of forming metal chelates with nuclides including, but not limited to, technetium, rhenium, cadmium, zinc, lead, silver, gold, gallium, platinum, palladium, rhodium, chromium, vanadium and the like.

The present invention also includes specific procedures for the chelation process between a nuclide and a ligand satisfying Formula II, thereby forming a metal chelate that has a chemical structure specified by Formula I.

It is further contemplated in this invention that the ligands of Formula II can be utilized for inhibiting metalloenzymes and for metal chelation, particularly chelation of toxic metals.

The present invention also provides kits that incorporate the features of the invention and makes possible a convenient means of practicing the invention. Kits of the invention comprise one or more compounds and/or compositions as described herein and may also include other materials that facilitate the practice of the invention, such as, but not limited to, instructions, descriptive indicators or labels, and devices relating to administration and/or use of the kit contents. The items comprising the kit may be supplied in the form of individual packages and/or packaged together, as desired by the skilled practitioner.

DETAILED DESCRIPTION OF THE INVENTION

The invention relates to the development of N,S-bidentate ligands. When developing effective, site-specific, therapeutic or diagnostic radiopharmaceuticals, many important factors may be considered. For example, it is important that the metallic radionuclide (e.g. Tc-99m)—upon interaction with a chelating agent—form an in vivo stable radiometal complex in high specific activities (e.g. Ci/μmol) with defined metal to ligand stoichiometry. These requirements have narrowed the choice to only a few ligand backbones. A detailed understanding of the coordination chemistry of new ligand systems with non radioactive rhenium or ground isotope Tc-99g is important for the subsequent extention of these reactions at the tracer levels in order to be able to label the chelating agents with Tc-99m. In addition, the ability of the ligand to form the radiometal complex under conditition amenable to routine formulation of radiopharmaceuticals is also an essential consideration.

Figure 1:
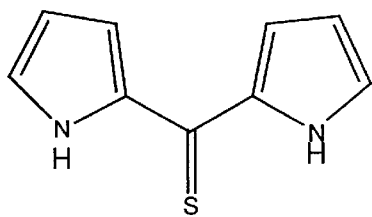
FIG. 1 shows the structure of a di-2-pyrrolylthione.

It was noted that di-2-pyrrolylthiones (see FIG. 1) form complexes with mercuric chloride, although no structures or characteristics of such complexes were provided (Clezy and Smythe, Aust. J. Chem. 22:239 (1969))

Brückner et al. tried to use di-2-pyrrolylthiones as starting materials for the synthesis of 5,15-diphenylporphyrin by means of the Raney-Nickel induced hydrodesulfirization of di-2-pyrrolylthione, thereby obtaining di-2-pyrrolylmethane—the key intermediate in the porphyrin synthesis (Brückner et al., *J. Porphyrins Phtalocyanines*, 2:455 (1998)). The anticipated hydrodesulfurization, however, did not occur; instead, a Ni(II)-2-pyrrolylthione complex was isolated from the reaction. The di-2-pyrrolylthionato complexes of Ni(II), Co(II), and Hg(II) were synthesized and characterized (Brückner et al., "Preparation and characterization of transition metal complexes of 2-pyrrolylthioketones" Abstract presented at Pacifichem 95 Conference, Honolulu, Hi., December 1995).

The present invention includes derivatives of 2-pyrrolylthione chelated to nuclides including, but not limited to: Cd, Pb, Zn, Ag, Au, Ga, Pt, Pd, Rh, Cr, V, Cu, and, most particurlarly, Tc and Re chelates.

Thus in a first aspect, the invention provides a metal chelate based on a 2-pyrrolylthione structure as shown in Formula I:

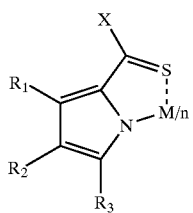

I wherein
M is independently selected from the group consisting of radioisotopes of Tc, Re, Cd, Pb, Zn, Ag, Au, Ga, Pt, Pd, Rh, Cr, Cu, V and the like;
n=1 to 4;
$R_1$, $R_2$, and $R_3$ is independently hydrogen, alkyl, OH or its derivative, halogen, $NO_2$, $NH_2$,
$N^+R_3$, NHCOR, CN, an alkyl carboxylic acid or acid ester group or its derivative, keto, $SO_3H$ or its derivative, or a group that, when taken together with another ring, ring substituent, forms a fused 5 or 6 membered ring, wherein R is independently hydrogen, alkyl, OH or its derivative, halogen, CN, an alkyl carboxylic acid or acid ester group or its derivative, keto, or $SO_3H$ or its derivative;
X is independently selected from the group consisting of unsubstituted or substituted alkyl or heteroalkyl, unsubstituted or substituted carbocycle, including aryl, unsubstituted or substituted heterocycle, AOH, ACOOH, ACOOR, AHal, CN, $ANO_2$, $ANH_2$, $ANR_2$, $AN^+R_3$, and ANHCOR wherein A is alkyl, heteroalkyl, carbocycle, including aryl or heterocycle, and R is alkyl or aryl and Hal is a halogen, preferably F, CL, Br, or I.

In preferred embodiments of the invention, n=2, and/or X is a pyrrole group, and/or X is a substituted or unsubstituted phenyl group. More preferably, X is a carboxymethyl substituted phenyl group. Preferably, $R_1$, $R_2$, and $R_3$ are not all H when X is an unsubstituted pyrrole group. Also preferred are embodiments where no more than one of $R_1$, $R_2$, and $R_3$ is a methyl when X is a methylated pyrrole group.

Definitions

Prior to further setting forth the invention, it may be helpful to an understanding thereof to first set forth definitions of certain terms that will be used hereinafter.

"Alkyl" is an unsubstituted or substituted, straight-chain or branched, saturated hydrocarbon; said hydrocarbon chain may have from 1 to about 8 carbon atoms. Preferred alkyl groups include, but are not limited to, methyl, ethyl, propyl, isopropyl, butyl, pentyl, hexyl, and heptyl groups. Other preferred alkyl chains for the practice of the invention have from about 2 to about 7, about 3 to about 6, and about 4–5 carbons.

"Heteroalkyl" is an unsubstituted or substituted, saturated chain having from 3 to 8 members and comprising carbon atoms and one or two heteroatoms. Preferred heteroalkyl groups include, but are not limited to, methyl, ethyl, propyl, isopropyl, butyl, pentyl, hexyl, and heptyl groups. Other preferred heteroalkyl chains for the practice of the invention have from about 2 to about 7, about 3 to about 6, and about 4–5 carbons.

"Heteroatom" is a nitrogen, sulfur or oxygen atom. Groups containing one or more heteroatoms may contain different heteroatoms.

"Carbocycle" as used herein is an unsubstituted or substituted, saturated, unsaturated or aromatic, monocyclic or polycyclic hydrocarbon ring. Preferred carbocyclic groups include, but are not limited to, unsubstituted or substituted phenyl rings.

"Heterocycle" as used herein is an unsubstituted or substituted, saturated, unsaturated or aromatic ring containing one or more heteroatoms in the ring. Preferred heterocycles include, but are not limited to, unsubstituted or substituted pyrrolyl, pyridyl, thiophenyl, tetrahydrofuranyl, morpholynyl, cumenyl and the like.

"Aryl" as used herein is an unsubstituted or substituted, organic group derived from an aromatic hydrocarbon by removal of one hydrogen.

"Substituted" as used herein refers to the presence of one or more heteroatoms and/or heteromoieties including, but not limited to, OH or its derivative, halogen (preferably F, CL, Br, or J), $NO_2$, $NH_2$, CN, an alkyl carboxylic acid or acid ester group or its derivative, keto, and $SO_3H$.

Figure 2:
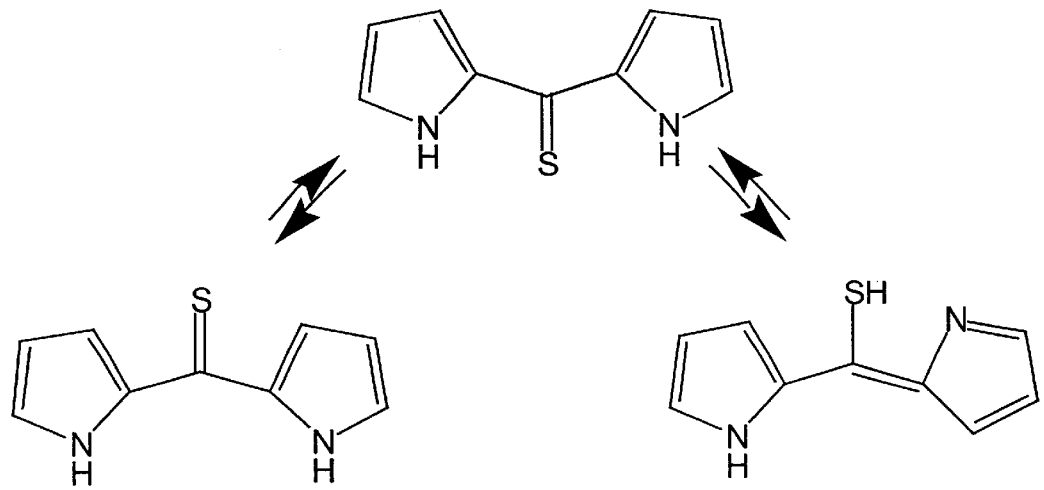
FIG. 2 shows tautomeric forms of di-2-pyrrolylthione.

Di-2-pyrrolylthione [number] could theoretically exist in various conformations, each in several tautomeric forms (see for example, FIG. 2).

The ability of 2-pyrrolylthiones to act as N,S-bidentate ligands and form stable metal complexes is derived from the ability of the pyrrolic group to release its electron density.

In one aspect of the present invention, two molecules of a 2-pyrrolylthione form symmetrical $N_2S_2$-core of the complex (n=2 in Formula I) with technetium and rhenium. Oxotechnetium and oxorhenium are readily chelated by this core.

A radiopharmaceutical of Formula I can be prepared from a 2-pyrrolylthione of the present invention by admixing at temperatures from 0° C. to 100° C. a salt of radionuclide M, a 2-pyrrolylthione and, optionally, a reducing agent in an aqueous solution or buffer, or in an organic solvent. Alternatively, a radiopharmaceutical of Formula I can be prepared by first admixing, at temperatures from 0° C. to 100° C., a salt of radionuclide M, an ancillary dioxygen ligand and, optionally, a reducing agent in an aqueous solution or buffer, or in an organic solvent, thereby forming an intermediate radionuclide complex with the ancillary ligands; then, a 2-pyrrolylthione ligand is added and the mixture is allowed to react further to form a 2-pyrrolylthionate via transchelation.

"Ancillary dioxygen ligands" include the ligands that coordinate the metal ion through at least two oxygen donor atoms. Examples include, but are not limited to: glucoheptonate, gluconate, 2-hydroxyisobutyrate, lactate, tartrate, mannitol, glucarate, Kojic acid, 2,2-bis (hydroxymethyl)propionic acid, 4,5-dihydroxy-1,3-benzene disulfonate, or substituted/unsubstituted 1,2- or 3,4-hydroxypyridinones, or pharmaceutically acceptable salts thereof.

Suitable "reducing agents" include, but are not limited to: stannous salts, dithionite or bisulfite salts, borohydride salts, and formamidine sulfinic acid—i.e. wherein the salts are of any pharmaceutically acceptable form.

"Buffers" useful in the preparation of radiopharmaceuticals of this invention are any that are pharmaceutically acceptable. These include, but are not limited to: phosphate, citrate, sulfosalicylate, and acetate.

Preferred radionuclides that can be used with the ligands of the present invention to synthesize radiopharmaceuticals can be selected from: Tc-99m, Re-186, or Re-188. For diagnostic purposes, Tc-99m is the preferred isotope. Its 6-hour half-life and 140 keV gamma-ray emission energy are considered ideal for gamma-scintigraphy when using equipment and procedures well established for those skilled in the art. The Re-isotopes also have gamma-ray emission energies which are compatible with gamma-scintigraphy. Re-186 and Re-188, however, also emit high-energy beta particles which are largely retained by living tissues. These beta emissions can be utilized for therapeutic purposes: e.g. cancer radiotherapy.

Preferably, the technetium and rhenium radionuclides are in the chemical form of pertechnetate or perrhenate plus a pharmaceutically acceptable cation. It is also preferable that the [$^{99m}$Tc]pertechnetate salt form is a sodium pertechnetate such as that which can be obtained from commercial Tc-99m generators. The amounts of pertechnetate used to prepare the Tc-99m-radiopharmaceuticals of the present invention can range from 0.1 mCi to 1 Ci; but, more preferably from 1 to 200 mCi.

The di-2-pyrrolylthione-based technetium and rhenium chelates encompassed by Formula I were synthesized and tested for renal uptake and clearance. For example, the technetium-99m chelates of Formula I wherein M=$^{99m}$TcO, $R_1$=$R_2$=H, and $R_3$=$SO_3H(Na)$ showed significant renal uptake and retention. Use of the Tc-99m-chelates of monosulfo-di-2-pyrrolylthione and disulfo-di-2-pyrrolylthione in rats demonstrated renal uptake, retention and comparable or superior quality of the renal images as were obtained with Tc-99m-DMSA (Technetium-99m Succimer Injection).

The amount of 2-pyrrolylthione reagents of the present invention used to prepare the Tc-99m-radiopharmaceuticals can range from 0.1 µg to 10 mg, or more preferably from 0.5 µg to 100 µg. The necessary amount is dictated by the amount of other reactants and the nature of the radiopharmaceutical to be prepared.

The total time of preparation can vary depending on the identity of the radionuclide, the nature and amounts of the reactants and the procedure used for preparation. The preparation may be complete after 1 min or it may require more time; upon completion, preparation will result in >80% yield of the radiopharmaceutical.

If a higher-purity radiopharmaceutical is required, the product can be purified by any of a number of techniques well known to those skilled in the art such as: liquid chromatography, solid phase extraction, dialysis and ultrafiltration.

Another aspect of the present invention is the formulation of radiopharmaceuticals to be used as renal imaging agents, which may be prepared in the form of diagnostic kits for clinical use. The sterile, non-pyrogenic formulation comprises a predetermined amount of the 2-pyrrolylthione ligand, and optionally other components such as reducing agents, transfer (or ancillary) ligands, saline or buffers, lyophilization aids, stabilization aids, solubilization aids and bacteriostats. The present invention also provides kits that incorporate the features of the invention and makes possible a convenient means of practicing the invention. Kits of the invention comprise one or more compounds and/or compositions as described herein and may also include other materials that facilitate the practice of the invention, such as, but not limited to, devices for administration and/or use of the compounds and/or compositions. The items comprising the kit may be supplied in the form of individual packages and/or packaged together, as desired by the skilled practitioner.

In one embodiment, a kit comprises at least one compound in a suitable container. Preferably, the kit contains at least an indication, such as, but not limited to, packaging or a label, identifying the kit, the compound as suitable for use in the applications described herein for the present invention and/or at least one instruction relating to the use of the kit or the compound in the applications described herein for the present invention. Optionally, the at least one instruction may be part of a larger set of instructions relating to the use of the kit or the compound in the applications described herein for the present invention or relating to the use of the kit or the compound in the practice of the present invention. Even more preferred are such kits indicated as suitable for use in humans and by way of the packaging, label, or instructions.

The renal imaging agent composition can be administered in a radioactive dose of about 0.01 mCi/mL to about 10 mCi/mL, most preferably about 2 mCi/mL to about 5 mCi/mL. The administration dose for a human patient is usually in the range of about 10 to about 30 mCi/mL. Actual dosages for different situations may of course be determined by the skilled practitioner without undue experimentation.

Formula I characterizes the present invention as being highly modifiable in order to tailor specifically the ligand for chelation with a defined radionuclide for localization at a target organ. The choice of a suitable type of complex with a given charge, or size of molecule, lipophilicity, etc., permits control over the following: the degree of plasma protein binding, cell permeation ability, clearance route of a drug, and other parameters important in radiopharmaceutical design.

Figure 3:
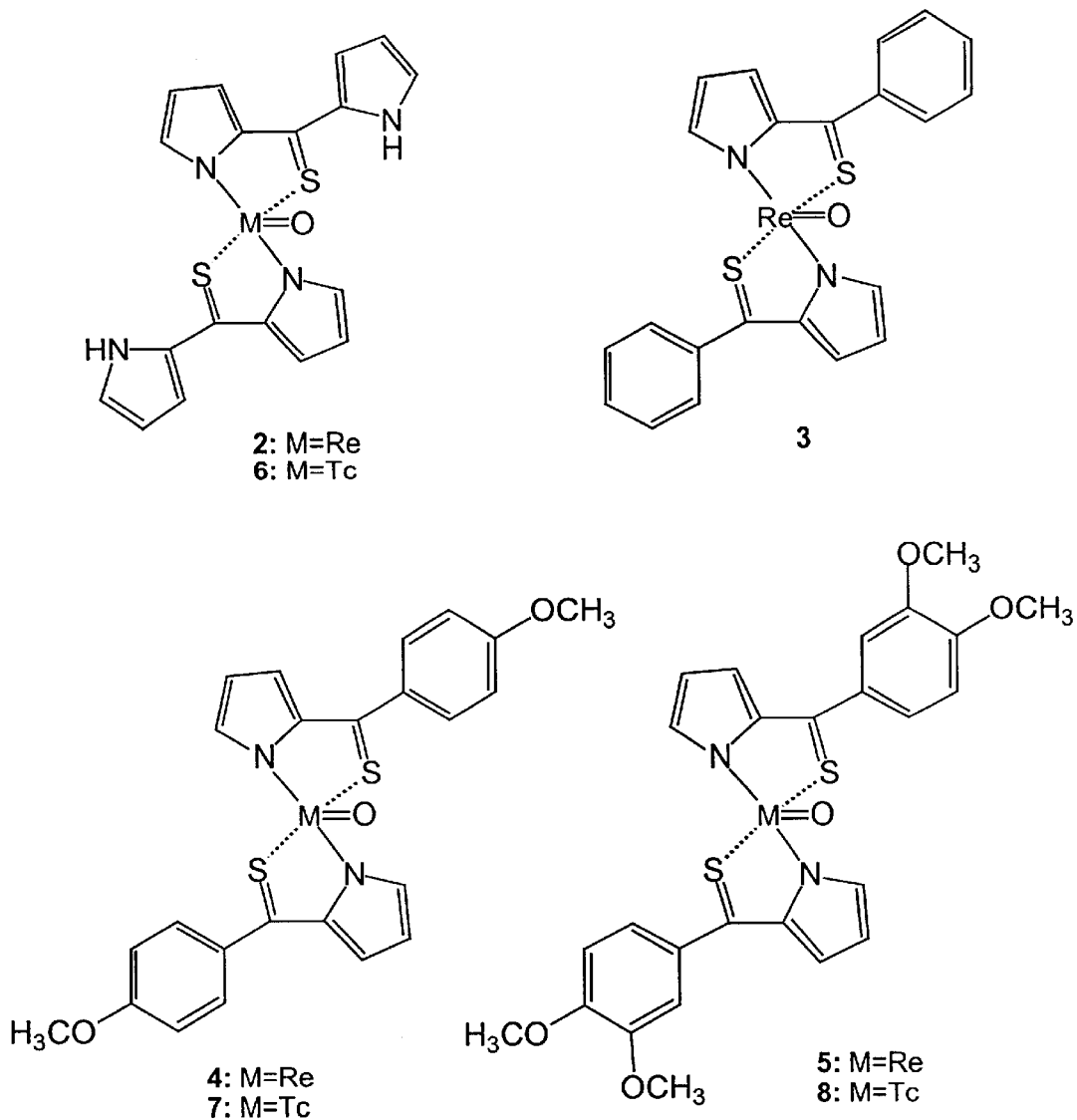
FIG. 3 shows lipophilic complexes of technetium and rhenium with 2-pyrrolylthiones.

For example, several lipophilic oxotechnetium and oxorhenium compounds 2–8 are presented in FIG. 3.

The compounds of the invention, as encompassed by Formula I, are not limited to the imaging of renal tissues and organs such as the kidney, but are suitable for imaging the organs and tissues of a higher organism generally. Examples of such organs include the heart, brain, and any other internal organ (see Dilworth et al., "The biomedical chemistry of technetium and rhenium. Chemical Society Reviews, 27:42–55 (1998)).

In one aspect of the present invention, it was found that reduced Tc-99g (the ground isotope pertechnetate) reacted smoothly with lipophilic 2-pyrrolylthione ligands in a methanolic solution, and formed with very few side products, within 5–30 min at 20–60° C., 2:1 complexes in high yields. In the case of oxorhenium species, the reaction takes longer to complete (up to 24 h) and needs to be conducted in oxygen-free media in order to prevent oxidation of Re(V). Various reducing agents listed above were used in these syntheses, with stannous chloride being the preferred one. Metal binding occurs at the pyrrolic nitrogen and sulfur atoms, leaving a pendant, uncoordinated pyrrolic or carbocyclic ring. These complexes are soluble in organic solvents such as chloroform and acetone. The oxotechnetium complexes, compounds 6, 7, and 8, are stable towards oxidation in solid state and in solution. The oxorhenium compounds, compounds 2–5, are less stable, although they can be kept in sealed vials for months.

Figure 4:
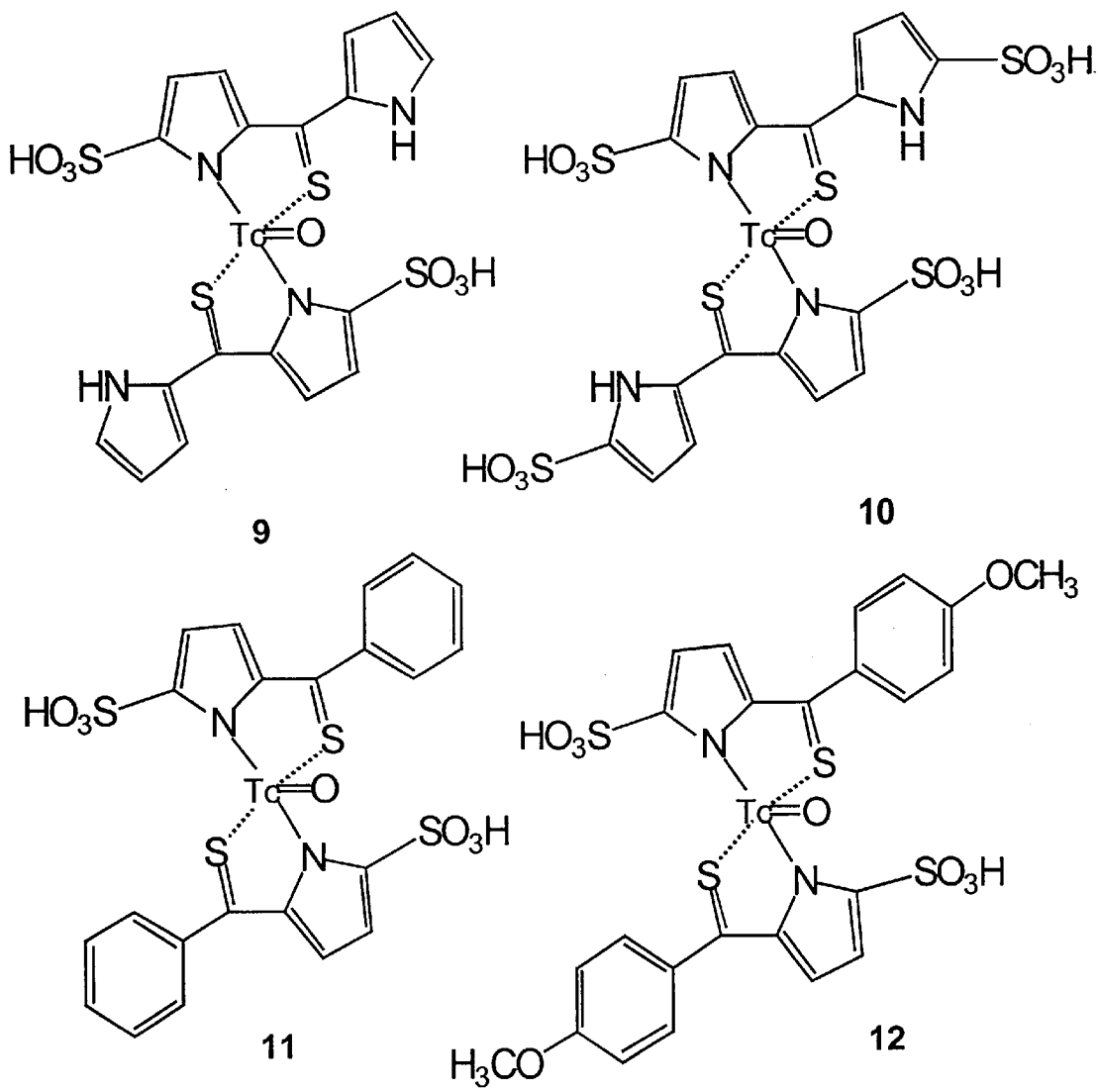
FIG. 4 shows water soluble complexes of technetium with 2-pyrrolylthiones. Tc indicates Tc-99g or Tc-99m.

To further illustrate the flexibility of this invention in terms of the variety of compounds it provides, a number of water soluble technetium complexes, compounds 9–12, are presented in FIG. 4.

Various pyrrolic-ring, pendant ring, and side-chain modifications are included as aspects of the present invention to make the chelate more polar and hydrophilic. Charged groups such as hydroxyl, carboxyl and sulfo groups can be added at the various positions on the periphery of the molecule to increase the hydrophilic character of the resulting chelate. Such structural modifications can cause more rapid and selective clearance from the bloodstream and from non-target tissue, as well as rapid uptake into kidney tissue.

The complexes of the ground isotope, Tc-99g, with 2-sulfopyrrolylthiones were prepared from [$^{99m}$Tc] pertechnetate, a reducing agent and a ligand in water or a buffer. Stannous chloride was the reducing agent of choice. Reduced pertechnetate reacts fairly smoothly with all ligands and forms stable 2:1 complexes. Thin layer chromatography (TLC) demonstrated that there was no starting material in the reaction mixture after it was heated at 60° C. for 15 min. Purification by normal or reverse phase column chromatography gave Tc-99g-complexes in good yields and with very few side products.

In a further aspect of the invention, the procedure is provided for the synthesis of radiometal complexes of sulfonated 2-pyrrolylthione ligands with metastable Tc-99m.

The reactions of corresponding sulfo-2-pyrrolylthione ligands with Tc-99m-pertechnetate were carried out in aqueous solutions or buffers. Stannous tartrate was selected as a preferred reducing agent. Labeling takes place within 1–30 min at 20–60° C. Normal or reverse-phase chromatography was used to purify and analyze the synthesized products. The analogous structure of Tc-99m-products was confirmed by comparing their chromatographic mobilities with those of Tc-99g-complexes.

The Tc-99m-complexes of sulfo-2-pyrrolylthiones were obtained with high radiochemical purity (>90%) and specific activity. The specific activity pertains to the ratio of molecules of radiochemical composition bearing Tc-99m to the total number of molecules of the composition. The high labeling efficiencies described in the examples below indicate that specific activity of the radionuclide is sufficiently high for use in significant radioactive quantity.

The complexes were formulated in a physiological solution for in vivo studies. The biodistribution and pharmacokinetics of these radiopharmaceuticals have been studied in male Sprague and Dawley rats, and the results are provided below. All Tc-99m-complexes tested were determined to be sufficiently stable in animal serum and in vivo to permit both completion of the preparation of the radiopharmaceutical and the thorough performance of a renal examination.

All the compounds in that study (see FIG. 4, Tc=Tc-99m) demonstrated significant and extremely rapid uptake into the kidney tissue. In particular, $^{99m}$TcO-disulfo-di-2-pyrrolylthionate, compound 9, and $^{99m}$TcO-tetrasulfo-di-2-pyrrolylthionate compound 10, showed very fast linear accumulation in the cortex (20% at 1.5 min post injection). Later, this accumulation persists and reaches its plateau at about 35 min to 1 hour post injection (at 22% the compound 9). The best excretion rate-as evaluated by measuring the activity found in the bladder—was obtained with compound 10.

From this set of data, it was concluded that Tc-99m-sulfo-2-pyrrolylthionates are suitable for use as radiopharmaceuticals for kidney imaging. They are comparable and, in certain aspects, superior to Tc-99m-DMSA (Technetium-99m Succimer Injection).

The present invention provides a series of ligands suitable for the formation of metal chelates disclosed under Formula I. These ligands are presented below according to Formula II.

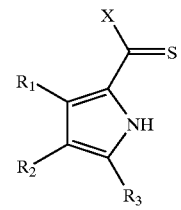

II wherein $R_1$, $R_2$, and $R_3$ is independently hydrogen, alkyl, OH or its derivative, halogen, $NO_2$, $NH_2$, $N^+R_3$, NHCOR, CN, an alkyl carboxylic acid or acid ester group or its derivative, keto, $SO_3H$ or its derivative, or a group that, when taken together with another ring, ring substituent, forms a fused 5 or 6 membered ring, wherein R is independently hydrogen, alkyl, OH or its derivative, halogen, CN, an alkyl carboxylic acid or acid ester group or its derivative, keto, or $SO_3H$ or its derivative;

X is independently selected from the group consisting of unsubstituted or substituted alkyl or heteroalkyl, unsubstituted or substituted carbocycle, including aryl, unsubstituted or substituted heterocycle, AOH, ACOOH, ACOOR, AHal, CN, $ANO_2$, $ANH_2$, $ANR_2$, $AN^+R_3$, and ANHCOR wherein A is alkyl, heteroalkyl, carbocycle, including aryl or heterocycle, and R is alkyl or aryl and Hal is a halogen, preferably F, CL, Br, or I.

Preferably, X is not an unsubstituted pyrrole group. Also preferred are embodiments where X is not a N-methylated pyrrole group or where no more than one of $R_1$, $R_2$, and $R_3$ is a methyl group.

The unsubstituted 2-pyrrolyl-phenylthione was previously described in the literature (Scheeren et al., *Chemical Communications*. (March issue): 149–151 (1973)).

The parent unsubstituted or substituted 2-pyrrolylketones served as precursors for the synthesis of ligands encompassed by Formula II. These novel 2-pyrrolylketones were obtained from pyrrole and corresponding Grignard derivatives using the method suggested in the literature (Pesson et al., *Chimie Therapeutique*.3:127–136 (1966)).

Synthesized 2-pyrrolylketones (containing carbonyl groups) were converted into 2-pyrrolylthiones (containing thione groups) of Formula II using either tetraphosphorus decasulfide ($P_4S_{10}$) or Lawesson's reagent (2,4-bis(4-methoxyphenyl)-1,3-dithia-2,4-diphosphetane-2,4-disulfide) (Brückner et al., 1998). The products were isolated by column chromatography in good yields, either as red crystalline solids or red oils, and were then thoroughly characterized. Substituted phenyl-2-pyrrolylthiones were found to have the same tautomeric nature as the di-2-pyrrolylthiones described above (see FIG. 2). Synthesized compounds show characteristic weak SH adsorption in their IR spectra near 2550 cm$^{-1}$, corresponding to the thiol tautomer, along with intense maxima at approximately 1035 cm$^-$, which represents the C=S stretching frequency. Without being bound by theory, this may explain their propensity to chelate the metals with large ionic radii and transition metals.

Another preferred embodiment of this invention provides a synthetic procedure designed to obtain the sulfonated 2-pyrrolylthione ligands which satisfy Formula II (wherein $R_1=R_2=H$ and $R_3=SO_3H$ or $SO_3Na$). The procedure disclosed in this embodiment involves mild sulfonation of corresponding precursors according to Formula I (wherein $R_1=R_2=R_3=H$) using 1,4-dioxane-sulfotrioxide as sulfonating agent and 1,4-dioxane as a solvent.

These reactions take place at room temperature and are usually completed in 10 min, thereby yielding a single product in the case of 2-pyrrolylthiones; and two major products when unsubstituted di-2-pyrrolylthione is used as a substrate (the products being mono- and disulfo-di-2-pyrrolylthione). The products are easily separated from the reaction mixture by means of extraction with acetone of the dry residue, which was obtained after evaporation of 1,4-dioxane. Chromatographical purification on the reverse-phase using water or a buffer as eluant furnished water-soluble sulfonated ligands obtained in high yields (>90%/o) as red crystalline solids.

In one aspect of this invention, it is contemplated that the complexes of Formula I, when M is beta-emitting Re-186 or Re-188, may be in treating cancer, coronary restenosis after percutaneous transluminal angioplasty, and other therapies. For example, it is possible that Re-analogs of compounds 9 and 10 could be used for teatment of medullary thyroid carcinoma, since these complexes have a biodistribution pattern similar to that of the rhenium complex of DMSA, which have been suggested for such treatment (P. J. Blower et al., J. Nucl. Med., 31:768 (1990)).

The metal chelates compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures.

The metal free compounds of the invention (see for example, Formula II) can be similarly formulated for use in the inhibition of metalloenzymes and for toxic metal chelation. The metalloenzymes subject to inhibition would be those that use metals subject to binding by the compounds of the invention. Presence of the compounds of the invention in contact with such metalloenzymes would result in the removal of the metals from availability to the metalloenzymes, thus inhibiting their activity. Metal free compounds of the invention may also be used to chelate metals from a solution, including toxic metals, thus making them unavailable or removable.

Generally, for the diagnosis or therapeutic applications, a compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the metal chelate compound to be administered depends upon the choice of metal isotope, the condition to be treated, the mode of administration, the individual subject, and the judgment of the practitioner. Depending on the specificity of the preparation, smaller or larger doses may be needed. For compositions that are highly specific to target tissues, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

Having now generally described the invention, the same will be more readily understood through reference to the following examples which are provided by way of illustration, and are not intended to be limiting of the present invention, unless specified.

EXAMPLES

Example 1

Synthesis of 2-pyrrolylthiones
p-Methoxyphenyl-2-pyrrylthione

A stirred solution of p-metoxyphenyl-2-pyrrylketone (4.02 g, 0.02 mol) in benzene (100 ml) was refluxed for 30 min under nitrogen. Tetraphosphorus decasulfide (4.44 g, 0.01 mol) was added gradually to the stirred solution over 30 min. The mixture was then allowed to react for 40 min. The excess of $P_4S_{10}$ was removed by filtration; the solvent was then evaporated; and, the residue was chromatographed on silica gel. Elution with toluene gave a bright scarlet fraction, which was collected to yield p-methoxyphenyl-2-pyrrolylthione as a bright red solid (2.81 g, 0.013 mol, 65% yield).

M.P.=97° C.

$^1$H NMR (CDCl$_3$): 9.81 (s, 1H), 7.80–7.79 (m, 1H,), 7.77–7.75 (m, 1H,), 7.28–7.26 (t, 1H), 6.93–6.92 (m, 1H), 6.90–6.88 (t, 1H), 6.76–6.74 (m, 1H), 6.41–6.38 (m, 1H), 3.87 (s, 3H) ppm.

$^{13}$C NMR (CDCl$_3$): 212.21, 162.37, 141.41, 139.20, 131.04, 129.57, 117.21, 113.17, 112.66, 77.44, 77.00, 76.56, 55.38, 29.57 ppm.

IR (KBr): 3784, 3403, 2977, 2838, 1599, 1527, 1503, 1389, 1337, 1303, 1257, 1173, 1107, 1036, 961, 836 cm$^{-1}$.

UV-Vis (CHCl$_3$), $\lambda_{max}$ (1 g $\epsilon$): 529 (2.69), 376 (4.38), 287 (3.57).

LR-MS, m/z: 217 (M$^+$).

Analysis: calculated for $C_{12}H_{11}NOS$: C, 66.34; H, 5.11; N, 6.45; S, 14.73; found: C, 66.56; H, 5.18; N, 6.40; S, 14.42.

3,4-Dimethoxyphenyl-2-pyrrolylthione

The method above afforded 3,4-dimethoxyphenyl-2-pyrrolylthione with a 45% yield. The compound was obtained as a bright red oil, which then crystallized upon standing. It is unstable at room temperature and is slowly oxidized by atmospheric oxygen.

MP=88–90° C.

$^1$H NMR (CDCl$_3$): 9.79 (s, 1H), 7.42–7.40 (m, 1H,), 7.38–7.37 (d, 1H,), 7.31–7.29 (t, 1H), 6.88–6.85 (d, 1H), 6.78–6.76 (m, 1H), 6.43–6.40 (m, 1H), 3.95 (s, 3H), 3.90 (s, 3H) ppm $^{13}$C NMR (CDCl$_3$): 139.28, 129.65, 122.58, 117.29, 112.77, 109.72, 77.37, 76.99, 76.56, 56.04, 29.65 ppm.

IR (KBr): 3783, 3403, 2969, 2840, 1593, 1513, 1461, 1415, 1383, 1331, 1266, 1170, 1142, 1109, 1036 cm$^{-1}$.

UV-Vis (CHCl$_3$), $\lambda_{max}$ (1 g $\epsilon$): 529 (2.59), 390 (4.29), 298 (3.59), 264 (3.90).

LR-MS, m/z: 247 (M$^+$).

Analysis: calculated for C$_{13}$H$_{13}$NO$_2$S: C, 63.14; H, 5.30; N, 5.66; S, 12.96; found: C, 63.24; H, 5.29; N, 5.30; S, 12.85.

Example 2

Sulfonation of 2-pyrrylthiones

General procedure. Solid 1,4-dioxanesulfotrioxide (2 mmol) was gradually added to the stirred solution of 2-pyrrolylthione (1 mmol) in 1,4-dioxane (25 ml) under nitrogen. The reaction mixture was allowed to stand during 10 min at room temperature. The solvent was then evaporated and the residue was dissolved in water (about 5 ml). The pH was brought to 4.5 using 1M solution of NaOH. Acetone (40 ml) was added and the white precipitate was separated by centrifugation. The red supernatant was then evaporated to dryness. Then, the solid product was chromatographed on reverse-phase using water as an eluant. The solvent was then evaporated leaving the hydrate of sodium salt of sulfonated 2-pyrrolylthione as a red crystalline solid. Single sulfonated derivatives resulted in all cases except 2,2'-dipyrrolylthione, wherein two products of sulfonation were found.

All synthesized sulfonated 2-pyrrolylthiones are highly soluble in water.

Monohydrate of sodium salt of phenyl-2-(4-sulfo) pyrrylthione.

$^1$H NMR (DMF-d$_7$): 11.81 (s, 1H), 7.69–7.66 (m, 2H), 7.60–7.50 (m, 2H), 7.48–7.45 (m, 2H), 6.75–6.76 (t, 1H) ppm.

$^{13}$C NMR (DMF-d$_7$): 214.80, 162.60, 138.00, 130.82, 130.69, 128.81, 128.30, 116.19 ppm.

IR(KBr): 3364, 3121 (ν(N—H)); 1615 (δ(C—H)$_{ar.}$); 1591, 1531, 1458 (ν(C—C)); 1408, 1367 (ν$_{as.}$(S(=O)$_2$)); 1320 (ω(C—N)); 1211 (ν(C=S)); 1155 (ν, (S(=O)$_2$)); 1113; 1082 (ar.); 1059 (ν(O-Na)); 1041; 1026 (ar.), 968, 941, 852 (ν(S—O—Na)); 768 (γ(C—H)); 700, 667 (γ(C—C), δ(C—H)); 644, 629, 617.

UV-Vis (H2O), $\lambda_{max}$ (1 gω): 513 (2.11), 382 (4.34), 320 (4.05), 215 (4.07).

LR-MS: 266 (M$^+$).

Analysis: calculated for C$_{11}$H$_{10}$NO$_4$S$_2$Na: C 42.99, H 3.28, N 4.56, S 20.86; found: C 42.32, H 2.73, N 4.41, S 20.44.

Trihydrate of sodium salt of p-methoxyphenyl-2-(4-sulfo) pyrrolylthione $^1$H NMR (DMF-d$_7$): 11.71 (s, 1H), 7.92–7.74 (m, 2H), 7.57–7.56 (m, 1H), 7.14–7.04 (m, 2H), 6.81–6.80 (m, 1H) ppm.

$^{13}$C NMR (DMF-d$_7$): 141.11, 139.94, 137.49, 131.27, 131.13, 129.72, 125.32, 124.15, 116.53, 115.55, 114.84, 114.06, 113.61, 55.63 ppm.

IR (KBr): 3570; 3283 (ν(N—H)); 1597, 1531, 1504, 1460 (ν(C—C)); 1408, 1367 (ν$_{as.}$(S(=O)$_2$)); 1310 (ω(C—N)); 1250 (ν$_{as.}$(C—O—C)); 1159 (V$_s$ (S(=O)$_2$)); 1117 (ar.); 1057 (ν(O—Na)); 1041; 1024 (ar., ν$_s$ (C—O—C)), 950, 941, 860, 837 (ν(S—O—Na)); 785 (γ(C—H)); 671, 635 (γ(C—C), γ(C—H)); 580.

UV-Vis (H2O), $\lambda_{max}$ (1 gω): ,: 511 (2.35), 375 (4.40), 221 (4.03).

LR-MS: 296 (M$^+$).

Analysis: calculated for C$_{12}$H$_{16}$NO$_7$S$_2$Na: C 38.60, H 4.32, N 3.75, S 17.17; found: C 38.75, H 3.63, N 3.69, S 17.38.

Monohydrate of sodium salt of 3,4-dimethoxyphenyl-2-(4-sulfo)pyrrylthione $^1$H NMR (DMF-d$_7$): 11.71 (s, 1H), 7.58–7.57 (m, 1H), 7.44–7.43 (m, 1H), 7.37–7.34 (m, 1H), 7.11–7.08 (m, 1H), 6.86–6.85 (m, 1H), 3.94 (s, 3H), 3.89 (s, 3H) ppm.

$^{13}$C NMR (DMF-d$_7$): 213.25, 152.69, 148.94, 139.94, 137.28, 129.67, 129.53, 122.60, 115.74, 113.48, 110.70, 55.89, 55.77 ppm.

IR (KBr): 3443(ν(N—H)); 3125 (ν(N—H)); 1595, 1531, 1512, 1462, 1454 (ν(C—C)); 1420, 1366 (V$_{as}$ (S(=O)$_2$)); 1331 (ω(C—N)); 1265 (V$_{as.}$(C—O—C)); 1210 (ν(C=S)); 1138 (ν$_s$(S(=O)$_2$)); 1043 (ν(O—Na)); 1016 (ν$_s$(C—O—C)); 941, 862 (ν(S—O—Na)); 762, 663, 635 (γ(C—H)); 478.

UV-Vis (H2O), $\lambda_{max}$ (1 gω): 508 (2.56), 382 (4.64), 264 (4.01), 221(4.34), (197 (4.54)?).

LR-MS: 326 (M$^+$).

Analysis: calculated for C$_{13}$H$_{13}$NO$_6$S$_2$Na: C 42.62, H 3.58, N 3.82; found: C 42.55, H 3.40, N 3.69.

Dihydrate of sodium salt of 2,2'-(4-sulfo)dipyrrylthione

This compound was obtained as a first product in the reaction of sulfonation of 2,2'-dipyrrylthione.

$^1$H NMR (DMF-d$_7$): 11.63 (s, 1H), 11.45 (s, 1H), 7.43–7.37 (m, 2H), 7.07–7.00 (m, 2H), 6.39–6.37 (m, 1H) ppm.

$^{13}$C NMR(DMF-d$_7$): 195.26, 139.62, 128.92, 126.92, 115.62, 112.90, 111.67 ppm.

IR (KBr): 3587, 3512, 3329, 3132 (ν(N—H)); 1631 (δ(C—H)); 1622 (δ(N—H)); 1529, 1462, 1404, 1350 (ν(C—C)); 1298, 1252 (ω(C—N)); 1211 (ν(C=S)); 1169 (ν(S(=O)$_2$)); 1121; 1099, 1059 (ν(O—Na)); 1028; 991, 945, 916, 879 (ν(S—O—Na)); 841, 752, 708, 677, 667, 631 (γ(C—H)); 586, 575, 542.

UV-Vis (H2O), $\lambda_{max}$ (1 gω): 397 (4.03), 224 (3.44).

LR-MS: 255 (M$^+$).

Analysis: calculated for C$_9$H$_9$N$_2$O$_4$S$_2$Na: C 34.39, H 3.53, N 8.91, S 20.40; found: C 35.06, H 2.94, N 8.93, S 19.84.

Dihydrate of sodium salt of 2,2'-(4,4'-disulfo)dipyrrylthione.

This compound was obtained as a second product in the reaction of sulfonation of 2,2'-dipyrrylthione.

$^1$H NMR (DMF-d$_7$): 11.71 (s, 2H), 77.44–7.43 (d, 2H), 7.37–7.33 (dd, 2H) ppm.

$^{13}$C NMR (DMF-d$_7$): 195.72,138.20,136.38, 127.19,112.90, 110.06ppm.

IR (KBr): 3468, 3122 (ν(N—H)); 2951, 1631 (6(C—H)); 1536, 1413, 1351 (ν(C—C)); 1218 (ν(C=S)); 1162 (V(S (=O)$_2$)); 1112; 1048 (ν(O—Na)); 939, 916, (ν(S—O—Na)); 834, 817(γ(C—H)).

UV-Vis (H2O), $\lambda_{max}$ (1 gω): 389 (4.44), 222 (3.76).

LR-MS: 335 (M$^+$).

Example 3

Syntheses of lipophilic Tc-99g and Re-complexes of 2-pyrrolylthiones (FIG. 3)

General procedure. A solution of SnCl$_2$ (0.5 mmol) in 0.6 N HCl (5 ml), purged with nitrogen, was added to a solution of a 2-pyrrolylthione (0.5 mmol) in EtOH (100 ml) under nitrogen atmosphere. The solution of KReO$_4$ or [$^{99g}$Tc] KtcO$_4$ (0.25 mmol) in water (10 ml) was added to this mixture. The reaction mixture was heated at 60° C. for 15–30 min. The solvent was then evaporated and the residue was treated with saturated aqueous solution of KHCO$_3$. Then the solid was separated by centrifugation and dissolved in an appropriate solvent for further purification by column chromatography.

Bis(2,2 '-dipyrrolylthionato) oxorhenium (compound 2) Purification: the residue solid was dissolved in acetone and 3 cm$^3$ of silica gel was then added to this solution. The solvent was carefully evaporated. The silica gel loaded with the compound was then placed on top of a silica gel column. Column chromatography (eluant: CHCl$_3$:EtOH=95:5) afforded bis(2,2'-dipyrrolylthionato)rhenium in 83% yield.

$^1$H NMR (Chloroform-d): 11.83 (s, 1H, N—H), 11.73 (s, 1H, N—H), 7.76 (s, 1H), 7.58 (s, 1H), 7.54–7.53 (m, 2H), 7.39–7.38 (d, 1H), 7.29–7.28 (d, 1H), 7.22–7.18 6.55 (m, 2H), 6.49–6.46 (m, 1H), 6.25–6.23 (m, 1H) ppm.

$^{13}$C NMR (Chloroform-d): 155.59, 155.11, 128.62, 123.57, 123.21, 119.12, 118.80, 118.62, 112.59 ppm.

UV-Vis (EtOH:DMF=50:1), $\lambda_{max}$ (1 g ω): 425 (3.97), 301 (3.31).

LR-MS, m/z: 553 (M$^+$).

Analysis: calculated for C$_{18}$H$_{14}$N$_4$OS$_2$Re·H$_2$O: C, 40.12; H, 3.37; N, 9.36; S, 10.71; found: C, 40.72; H, 3.29; N, 9.10; S, 10.62.

Bis(phenyl-2-pyrrolylthionato) oxorhenium (compound 3)

Purification: flash chromatography on silica gel with chloroform. Yield: 40%.

$^1$H NMR (Chloroform-d): 7.97–7.53 (m, 6H), 7.30–7.06 (m, 1H), 6.78–6.38 (m, 1H) ppm.

$^{13}$C NMR (Chloroform-d): 160.55, 132.25, 131.96, 130.35, 129.07, 127.91, 122.26, 121.73 ppm.

UV-Vis (Chloroform), $\lambda_{max}$ (1 g ω): 454.5 (4.28), 335.5 (5.18).

LR-MS, m/z: 575 (M$^+$).

Analysis: calculated for C$_{22}$H$_{16}$N$_2$OS$_2$Re: C$_2$H$_5$OH: C, 46.44; H, 3.57; N, 4.51; S, 10.33; found: C, 46.63; H, 3.28; N, 4.31; S, 10.35.

Bis(p-methoxyphenyl-2-pyrrolylthionato) oxorhenium (compound 4)

Purification: column chromatography (0–2% ethanol in chloroform) followed by reprecipitation from hexane gave bis(p-methoxyphenyl-2-pyrrolylthionato) rhenium in 69% yield.

$^1$H NMR (Chloroform-d): 8.03–7.51 (m, 3H), 7.11–6.55 (m, 3H), 4.23–4.19 (m, 1H), 3.98–3.71 (m, 3H, —CH$_3$) ppm.

UV-Vis (Chloroform), $\lambda_{max}$ (1 g ω): 382 (4.39).

LR-MS, m/z: 635 (M$^+$).

Analysis: calculated for C$_{24}$H$_{20}$N$_2$O$_3$S$_2$Re·C$_2$H$_5$OH: C, 45.87; H, 3.85; N, 4.11; S, 9.42. found: C, 47.09; H, 3.63; N, 3.82; S, 9.32.

Bis(3,4-dimethoxyphenyl-2-pyrrolylthionato) oxorhenium (compound 5)

Purification: normal phase column chromatography (2–20% ethanol in chloroform) and reprecipitation from hexane. Yield: 75%.

$^1$H NMR (Chloroform-d): 7.74 (s, 1H), 7.42–7.40 (m, 1H), 7.28–7.24 (m, 1H), 7.13–7.10 (m, 1H), 6.73–6.70 (d, 1H), 6.63–6.61 (m, 1H), 4.05–4.01 (m, 3H), 3.99–3.92 (m,3H), 1.56 (s, 2H), 1.25 (s, 3H).

$^1$C NMR (Chloroform-d): 158.76, 151.63, 126.94, 124.04, 123.47, 120.03, 113.39, 112.89, 110.23, 109.87, 56.13, 55.86, 29.73 ppm.

UV-Vis (Chloroform), $\lambda_{max}$ (1 g ω): 432 (4.24), 352 (4.09), 268 (4.16), 243 (4.21).

LR-MS, m/z: 695 (M$^+$).

Analysis: calculated for C$_{26}$H$_{24}$N$_2$O$_4$S$_2$Re·2H$_2$O: C, 46.74; H, 4.71; N, 3.63; S, 8.32, found: C, 46.73; H, 4.37; N, 3.56; S, 8.09.

Bis(2,2'-dipyrrolylthionato) $^{99}$g Tc]oxotechnetium (compound 6)

Purification: column chromatography on silica gel (0–30% methanol in chloroform) gave pure complex in 89% yield.

$^1$H NMR (Chloroform-d): 11.74 (s, 1H, N—H), 8.35 (s, 1H), 8.02 (s, 1H), 7.51 (s, 1H), 7.31–7.25 (m, 1H), 7.17 (s, 1H), 6.53 (s, 1H) ppm.

UV-Vis (Ethanol), $\lambda_{max}$ (1 g ε): 429 (4.03).

LR-MS, m/z: 465 (M$^+$).

Bis(p-methoxyphenyl-2-pyrrolylthionato) [$^{99}$g Tc]oxotechnetium (compound 7)

Purification: column chromatography on silica gel (2–30% ethanol in chloroform) followed by reprecipitation from hexane. Yield: 41%.

$^1$H NMR (Chloroform-d): 8.04–6.23 (m, 7H), 3.94–3.81 (m, 3H) $^{13}$C NMR (Chloroform-d): 132.21, 131.17, 130.01, 113.57, 55.40, 33.62, 31.85, 29.64, 29.27, 29.00, 24.65, 22.66, 14.06 ppm.

UV-Vis (Chloroform), $\lambda_{max}$ (1 g ω): 696 (3.01), 368 (4.27).

LR-MS, m/z: 547 (M$^+$).

Bis(3,4-dimethoxyphenyl-2-pyrrolylthionato) [99g Tc]oxotechnetium (compound 8)

Purification: column chromatography on silica gel (eluent CHCl$_3$: EtOH=4:1) followed by reprecipitation from hexane gave fine black precipitate of target compound. Yield:43%.

$^1$H NMR (Chloroform-d): 7.70–6.34 (m, 6H), 4.23–3.78 (m, 6H), 1.70–1.25 (m, 10H), 0.94–0.87 (m, 2H) ppm.

$^{13}$C NMR (Chloroform-d): 131.48, 130.89, 128.84, 126.04, 124.50, 123.75, 123.31, 121.63, 112.94, 111.57, 110.99, 110.09, 56.32, 56.05, 29.72 ppm.

UV-Vis (Chloroform), $\lambda_{max}$ (1 g ω): 328 (4.23).

LR-MS, m/z: 607 (M$^+$).

Example 4

Labeling of water soluble 2-pyrrolylthiones with Tc-99m

General Procedure.

A 2-pyrrolylthione ligand (0.2 mg) was dissolved in 1 ml of water. Fresh saturated aqueous solution of stannous tartrate (200 μL) was added, followed by 1–10 mCi of sodium [$^{99m}$Tc]pertechnetate in 0.2–0.5 mL of saline (eluate from the generator). The mixture was purged with nitrogen and incubated at 60° C. for 15 min. The end of reaction was monitored by means of thin layer chromatography using silica gel impregnated paper strips (Whatman). A well dried spot from the reaction mixture was run, successively, with acetone (to detect free pertechnetate, R$_f$=1), then with methanol (to detect the complex (R$_f$=1) and reduced technetium (R$_f$=0). The quantitative data obtained with paper chromatography showed the labeling efficiency >90% for all the ligands.

The reaction mixture was then stripped of solvent in vacuo, the residue was then re-dissolved in ethanol or water and purified using either normal phase Seppak cartriges (Waters), conditioned with ethanol, or Cephadex G-10. Finally, a purified Tc-99m-complex was re-dissolved in saline (1–10 mL depending on the dosage required for injection).

Example 5

Renal Imaging

General Procedure.

A group of 3 male Sprague and Dawley rats were anaesthetised by intra-muscluar administration of a mixture of Ketamine Xylazine (1 ml/Kg). A 26 guage Butterfly was introduced into the lateral tail vein and filled with heparinised physiological saline. The animals were injected with the indicated radiopharmaceutical, in the minutes following the beginning of the acquisition.

Dose activities were measured in an Accucal 2001 dose calibrator Nuclear Pharmacy Inc. (Albuquerque, N. Mex., U.S.A). Scvintigraphic mages were recorded with a Starcam 4000i XRT Gamma camera General Electric (Saint Albans, UK) equipped with a parallel, medium energy, high resolution collimator. Image analysis was performed on a Genie PNR model nuclear medicine dedicated computer General Electric (Saint Albans, UK).

Data on the rats, compounds, and scans used are summarized in Table 1 below. TcSL11 and TcSL12 refer to compounds 9 and 10, respectively.

TABLE 1

| rat i.d. | Weight Kg | Activity/volume | Compound | Position on the scans |
|---|---|---|---|---|
| A | 0.292 | 18 MBq/0.5 ml | TcSL11† | Left |
| B | 0.304 | 18 MBq/0.5 ml | TcSL12‡ | Middle |
| C | 0.306 | 16 MBq/0.5 ml | DMSA• | Right |

†[$^{99m}$Tc] TcSL11 (tetrasulfo-) (1c) 103 Mba in ~ 1.5 ml.
‡†[$^{99m}$Tc] TcSL12 (disulfo-) (1f) 103 Mba in ~ 1.5 ml.
•Freshly prepared 99mTc-DMSA, "Technetium (Tc-99m) Succimer Injection" kit Nordion Europe SA.

The camera was set to record a series of 32 images at 1 min intervals each, the animals were injected successively starting from animal A after the camera was started. All injections were finished within the first one and a half minute. Following each injection the catheter was flushed with 0.5 ml of physiological saline. Following this first acquisition a second dynamic acquisition was recorded at a rate of one image every 10 minutes. The animals woke up 90 min after injection at which time the study was terminated.

For analysis, the areas of interest were traced around the organs of interest (right and left kidneys for the first dynamic study; and heart, left kidney and bladder at image 60 min. post-injection on the second study) and the whole body of the rats. The result were expressed as counts per seconds or as percent of the whole body activity at a given time, and are presented in FIGS. 5–9.

Figure 5:
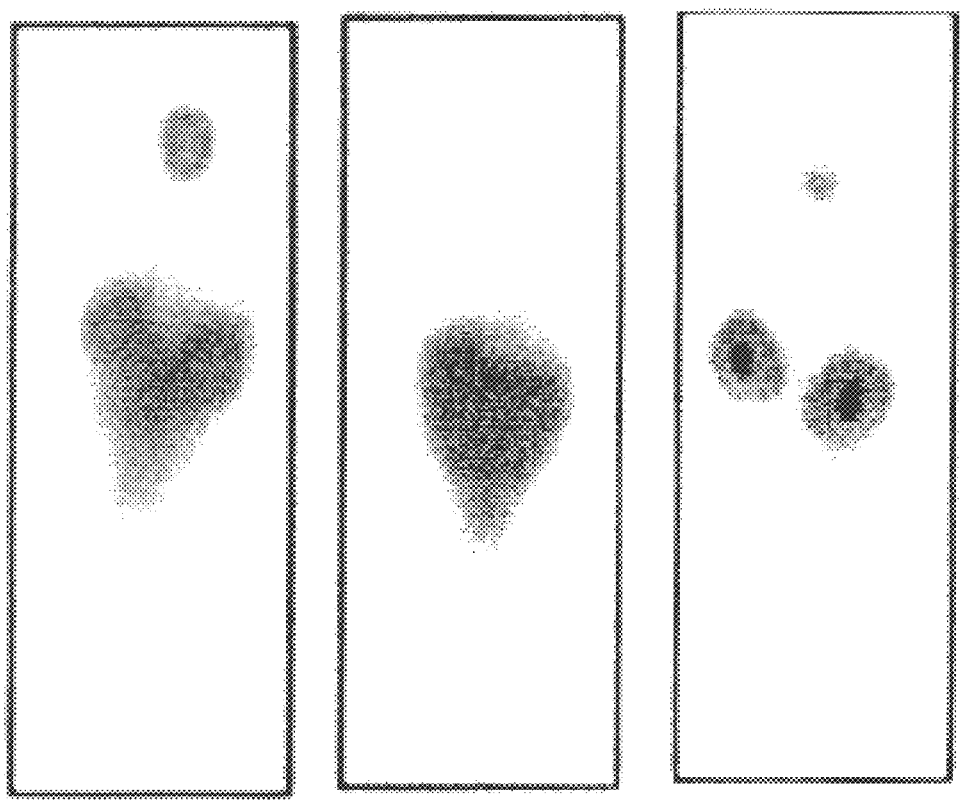
FIG. 5 shows scintigraphic images of biodistributed radioactivity in rats at one hour post injection. The rats are upside down with the bladder being at the top of each image. From left to right are TcSL11 (compound 9), TcSL12 (compound 10), and DMSA.

FIG. 5 shows scintigraphic images from the rats used. Application of TcSL-11 better resolved the kidneys, where the liver is still apparent, than with TcSL-12. With both TcSL-11 and Tc-DMSA the kidneys are well visualised, with the outer area the cortex appearing as a dark band delimiting the kidney whereas the medulla is greyish. With the DMSA however the innermost par of the kidney (kidney pelvis, calyx area) where the urine is collected is better defined.

Figure 6:
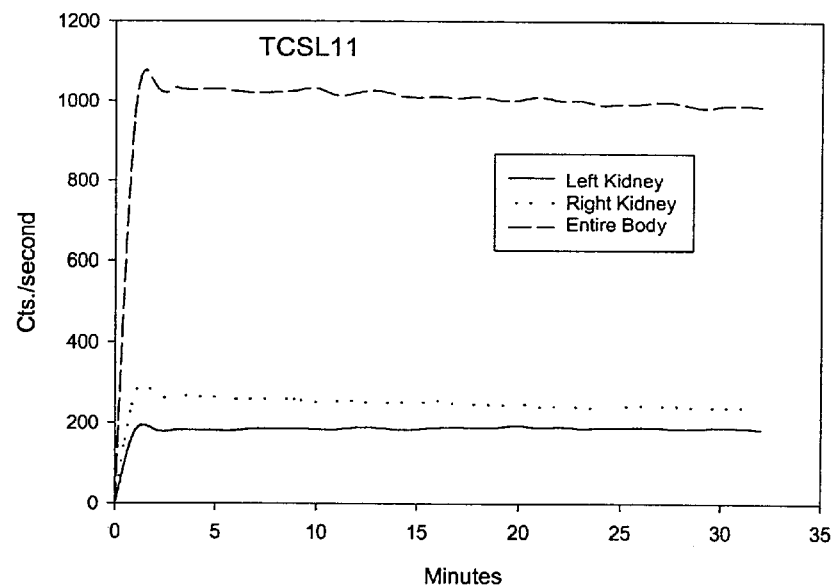
FIG. 6 shows radioactivity distribution curves for TcSL11 in the kidneys and whole body of a treated rat.
Figure 6:
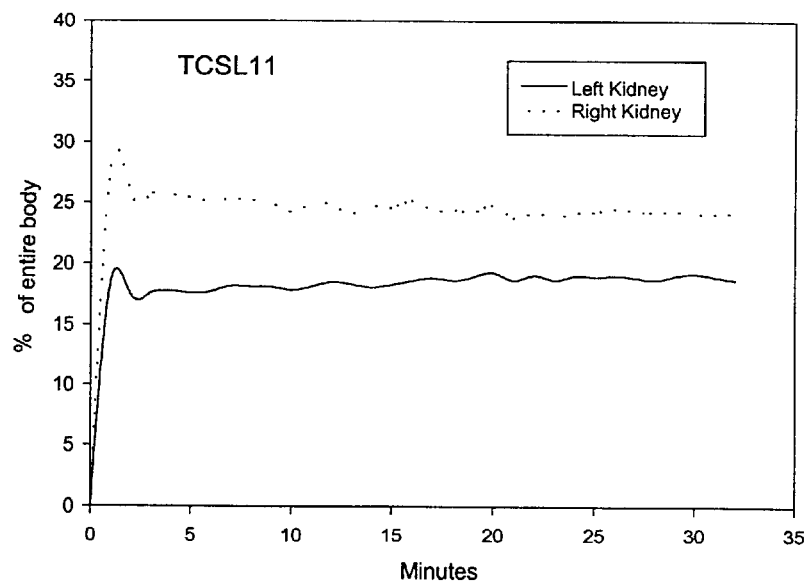
Figure 7:
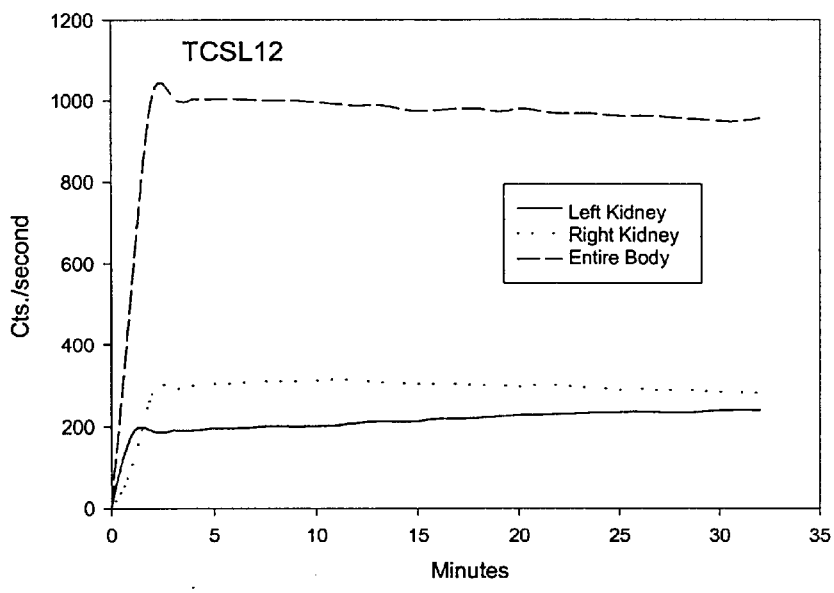
FIG. 7 shows radioactivity distribution curves for TcSL12 in the kidneys and whole body of a treated rat.
Figure 7:
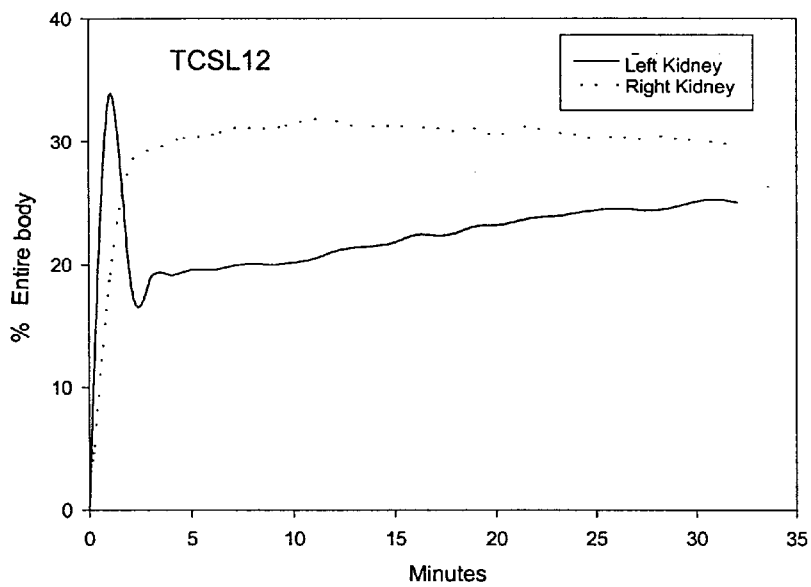
Figure 8:
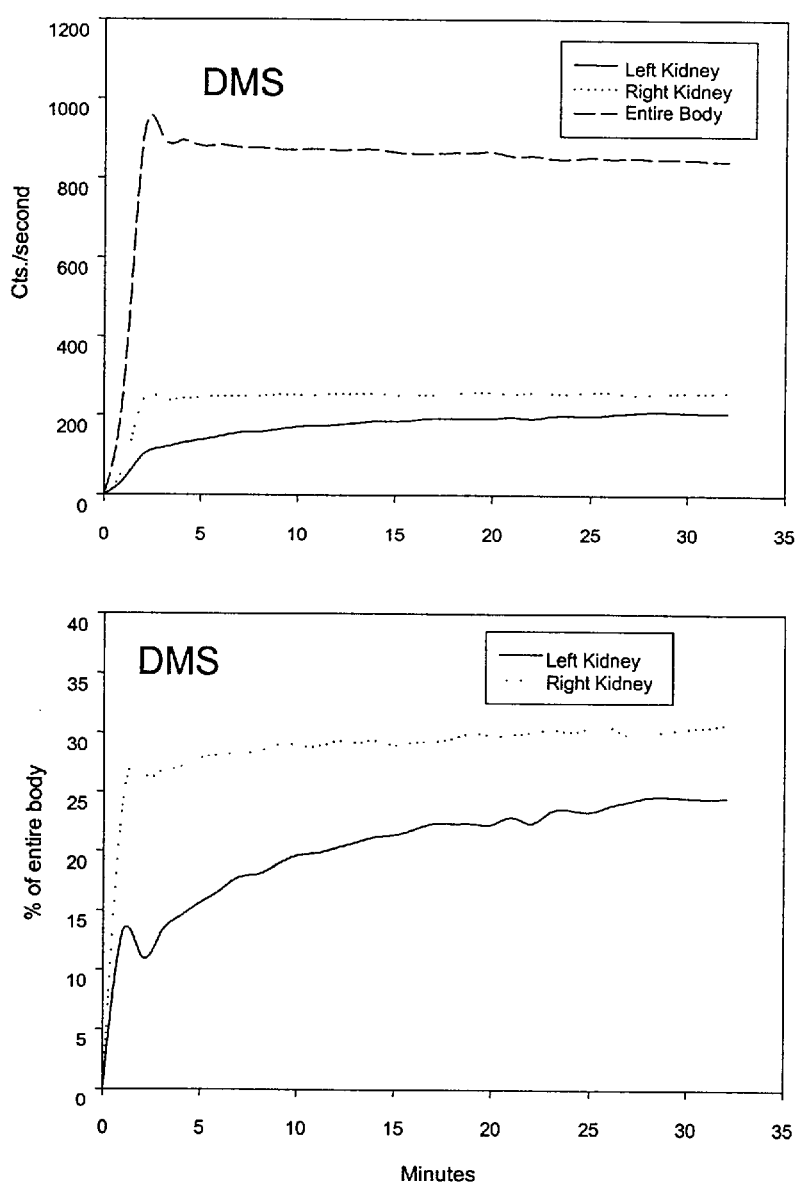
FIG. 8 shows radioactivity distribution curves for DMSA in the kidneys and whole body of a treated rat.

FIGS. 6–8 show plots of relating the various imaging agents in the treated rats over time. As indicated, the detected radioactivity in the kidneys reach a plateau more rapidly with TcSL-11 as compared to DMSA. This is one advantage provided by the present invention.

Figure 9:
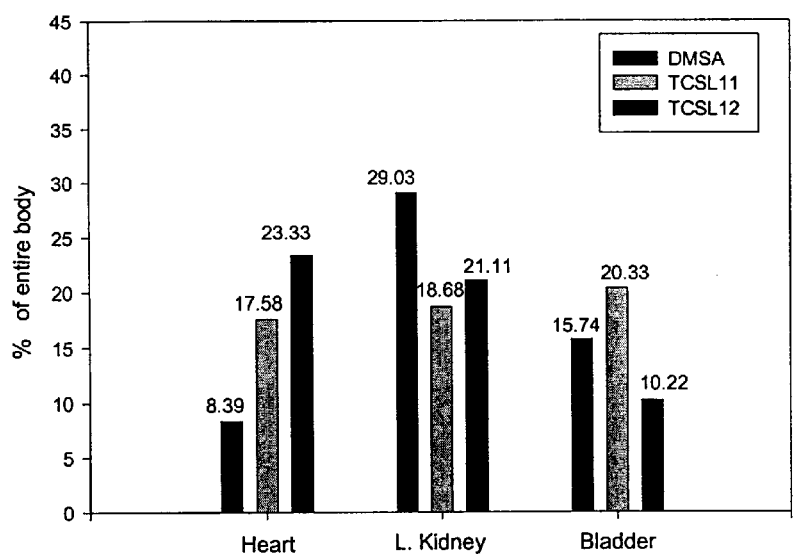
FIG. 9 shows a plot of radioactivity distribution in select rat tissues one hour post injection.

Biodistribution at 1 hour post-injection is shown in FIG. 9. If the heart area is used as a measure of blood activity, it is seen that DMSA is more rapidly cleared, followed by TcSL-11 and TcSL-12. As far as overall kidney uptake is concerned, DMSA show the highest activity followed by TcSL-11 and 12 which show similar values. It should be noted, however, that with DMSA there is significant activity in the calyx area. For kidney uptake only the left kidney was considered as the right kidney was positioned under the liver. The best excretion rate as evaluated by measuring the activity found in the bladder was obtained with TcSL-11. Thus TcSL-11 is comparable and in certain aspect superior to DMSA.

It is expected that the imaging metal chelate agents of the invention would be useful in specific pathologies where DMSA has been used, as well as in situations where the present invention would be expected to provide advantages.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A diagnostic imaging or therapeutic agent having the formula:

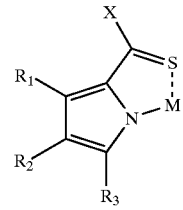

wherein
M is independently selected from the group consisting of radioisotopes of Tc, Re, Cd, Pb, Zn, Ag, Au, Ga, Pt, Pd, Rh, Cr, Cu, V and the like; and
wherein from 1 to 4 chelating moieties having the structure

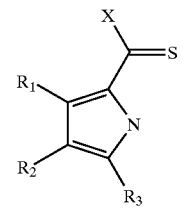

are bound to said M; and
wherein each of $R_1$, $R_2$, and $R_3$ is independently hydrogen, alkyl, OH or its derivative, halogen, $NO_2$, $NH_2$, $N^+R_3$, NHCOR, CN, an alkyl carboxylic acid or acid ester group or its derivative, keto, $SO_3H$ or its derivative, or a group that, when taken together with another ring, ring substituent, forms a fused 5 or 6 membered ring, wherein R is independently hydrogen, alkyl, OH or its derivative, halogen, CN, an alkyl carboxylic acid or acid ester group or its derivative, keto, or $SO_3H$ or its derivative; and
wherein X is independently selected from the group consisting of unsubstituted or substituted alkyl or heteroalkyl, unsubstituted or substituted carbocycle, including aryl, unsubstituted or substituted heterocycle, AOH, ACOOH, ACOOR, AHal, CN, $ANO_2$, $ANH_2$, $ANR_2$, $AN^+R_3$, and ANHCOR wherein A is alkyl, heteroalkyl, or carbocycle, including aryl or heterocycle and R is alkyl or aryl and Hal is a halogen, preferably F CT, Br or I.

2. The agent of claim 1 wherein M is Tc or Re.

3. The agent of claim 2 wherein M is Tc.

4. The agent of claim 3 wherein said Tc is technetium-99m.

5. The agent of claim 1 wherein $R_3$ is $SO_3H$ or the salt thereof.

6. The agent of claim 5 wherein said salt is Na.

7. The agent of claim 1 wherein 2 chelating moieties are bound to said M.

8. The agent of claim 1 wherein X is a pyrrole group.

9. The agent of claim 1 wherein X is a substituted or unsubstituted phenyl group.

10. The agent of claim 9 wherein X is a carboxymethyl substituted phenyl group.

11. A pharmaceutical composition comprising an agent of any one of claims 1 to 10.

12. A method of imaging tissue comprising visualizing said tissue after administration of an agent according to any one of claims 1 to 10.

13. The agent of claim 1 wherein said carbocycle is aryl or heterocycle.

14. The agent of claim 1 wherein Hal is F, Cl, Br, or I.

15. A diagnostic imaging or therapeutic agent having the formula:

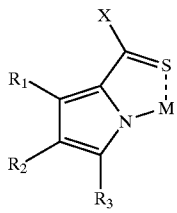

wherein
  M is independently selected from the group consisting of radioisotopes of Tc, Re, Cd, Pb, Zn, Ag, Au, Ga, Pt, Pd, Rn, Cr, Cu, and V; and
  wherein from 1 to 4 chelating moieties having the structure

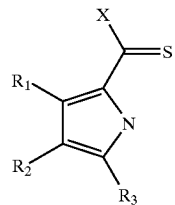

are bound to said M;
  wherein each of $R_1$, $R_2$, and $R_3$ is independently hydrogen, alkyl, OH, halogen, $NO_2$, $NH_2$, $N^+R_3$, NHCOR, CN, an alkyl carboxylic acid or acid ester group, keto, $SO_3H$, or a group that, when taken together with another ring, ring substituent, forms a fused 5 or 6 membered ring, wherein R is independently hydrogen, alkyl, OH, halogen, CN, an alkyl carboxylic acid or acid ester group, keto, or $SO_3H$; and
  wherein X is independently selected from the group consisting of alkyl or heteroalkyl, carbocycle, heterocycle, AOH, ACOOH, ACOOR, AHal, CN, $ANO_2$, $ANH_2$, $ANR_2$, $AN^+R_3$, and ANHCOR wherein A is alkyl, heteroalkyl, or carbocycle, and R is alkyl or aryl and Hal is a halogen.

16. A pharmaceutical composition comprising an agent of any one of claims 13 to 15.

17. A method of imaging tissue comprising visualizing said tissue after administration of an agent according to any one of claims 13 to 15.

18. A method of imaging tissue comprising visualizing said tissue after administration of a composition according to claim 11.

19. A method of imaging tissue comprising visualizing said tissue after administration of a composition according to claim 16.

* * * * *